United States Patent [19]
Broeker et al.

[11] Patent Number: 6,137,001
[45] Date of Patent: Oct. 24, 2000

[54] PROCESS FOR PREPARING AROMATIC CARBOXYLIC ACIDS WITH EFFICIENT TREATMENTS OF GASEOUS EFFLUENT

[75] Inventors: Jeffrey L. Broeker, Channahon; Frank G. Belmonte, Norwood Park; Thomas M. Bartos, Naperville; Alakananda Bhattacharyya, Glen Ellyn; Anne M. Karachewski, St. Charles; Bruce I. Rosen, Morton Grove; Kenneth J. Abrams, Naperville, all of Ill.

[73] Assignee: BP Amoco Corporation, Chicago, Ill.

[21] Appl. No.: 09/245,214

[22] Filed: Feb. 5, 1999

Related U.S. Application Data

[60] Provisional application No. 60/074,371, Feb. 11, 1998.

[51] Int. Cl.[7] .................................................. C07C 51/15
[52] U.S. Cl. .............................................................. 562/413
[58] Field of Search .............................................. 562/413

[56] References Cited

U.S. PATENT DOCUMENTS

| | | |
|---|---|---|
| 4,317,919 | 3/1982 | Jones et al. . |
| 4,356,159 | 10/1982 | Norval et al. . |
| 4,471,619 | 9/1984 | Nolley, Jr. . |
| 4,826,600 | 5/1989 | Ely et al. . |
| 4,914,230 | 4/1990 | Abrams et al. . |
| 4,966,611 | 10/1990 | Schumacher et al. . |
| 5,050,375 | 9/1991 | Dickinson . |
| 5,102,505 | 4/1992 | Sorensen . |
| 5,235,117 | 8/1993 | Alagy et al. . |
| 5,463,113 | 10/1995 | Yamamoto et al. . |
| 5,612,007 | 3/1997 | Abrams . |
| 5,723,656 | 3/1998 | Abrams . |

FOREIGN PATENT DOCUMENTS

| | | |
|---|---|---|
| 498591 A2 | 3/1992 | European Pat. Off. . |
| 2187732 | 6/1972 | France . |
| 2303787 | 3/1975 | France . |
| 5599517 | 1/1979 | Japan . |

OTHER PUBLICATIONS

Abstract: *Energy conservation at Amoco Chemicals*, J. Reumers, vol. 25, No. 3, 1984 pp. 165–167.

*Primary Examiner*—Paul J. Killos
*Attorney, Agent, or Firm*—Wallace L. Oliver; Phyllis Turner-Brim

[57] ABSTRACT

Processes are disclosed for recovery of hydrogen bromide from one or more alkyl bromide compounds by hydrolyzing the alkyl bromide compounds to hydrogen bromide and corresponding alcohols, and simultaneously separating at least the alcoholic products of hydrolysis from aliphatic monocarboxylic acid solvent component. Also disclosed are process for preparing aromatic carboxylic acids by the exothermic, liquid-phase oxidation of an aromatic feedstock compound wherein the energy produced by the exothermic oxidation is efficiently recovered, and uses of water produced during the preparation of aromatic carboxylic acids are efficiently integrated into the process.

20 Claims, 2 Drawing Sheets

PROCESS FOR PREPARING AROMATIC CARBOXYLIC ACIDS WITH EFFICIENT TREATMENTS OF GASEOUS EFFLUENT

CROSS-REFERENCE TO RELATED APPLICATIONS

This application claims benefit and priority of U.S. Provisional Application Ser. No. 60/074,371 filed Feb. 11, 1998 which is incorporated in its entirety herein by reference.

FIELD OF THE INVENTION

This invention relates to an improved method for handling alkyl bromide compounds that are produced as co-products during exothermic, liquid-phase oxidation of aromatic feedstock compounds to aromatic carboxylic acids. More particularly, this invention relates to a process for recovery of hydrogen bromide from alkyl bromide compounds by hydrolysis to hydrogen bromide and corresponding alcohols, and simultaneously separating at least the alcoholic products of the hydrolysis from an aliphatic monocarboxylic acid solvent component. This invention also relates to a process for preparing aromatic carboxylic acids by the exothermic, liquid-phase oxidation of an aromatic feedstock compound wherein the energy produced by the exothermic oxidation is efficiently recovered, and uses of water produced during the preparation of aromatic carboxylic acids are efficiently integrated into the process.

BACKGROUND OF THE INVENTION

Aromatic carboxylic acids are useful chemical compounds and are raw materials for a wide variety of manufactured articles. For example, terephthalic acid is manufactured on a world-wide basis in amounts exceeding 10 billion pounds per year. A single manufacturing plant can produce 100,000 to more than 750,000 metric tons of terephthalic acid per year. Terephthalic acid is used, for example, to prepare polyethylene terephthalate, a raw material for manufacturing polyester fibers for textile applications and polyester film for packaging and container applications. Terephthalic acid can be produced by the high pressure, exothermic oxidation of a suitable aromatic feedstock compound, such as para-xylene, in a liquid-phase reaction using air or other source of dioxygen (molecular oxygen) as the oxidant and catalyzed by one or more heavy metal compounds and one or more promoter compounds.

Methods for oxidizing para-xylene and other aromatic compounds using such liquid-phase oxidations are well known in the art. For example, Saffer in U.S. Pat. No. 2,833,816 discloses a method for oxidizing aromatic feedstock compounds to their corresponding aromatic carboxylic acids. Central to these processes for preparing aromatic carboxylic acids is employing an oxidation catalyst comprising a heavy metal component and a source of bromine in a liquid-phase reaction mixture including a low molecular weight monocarboxylic acid, such as acetic acid, as part of the reaction solvent. A certain amount of water is also present in the oxidation reaction solvent and water is also formed as a result of the oxidation reaction. Although various means can be used to control the temperature of the highly exothermic oxidation reaction, it is generally most convenient to remove heat by allowing the solvent to vaporize, i.e. boil, during the oxidation reaction. Gaseous effluent from the oxidation reaction generally comprises steam, monocarboxylic acid, an ester thereof, carbon dioxide, carbon monoxide and bromine which, depending on the aromatic feedstock compound used, is mainly in the form of one or more alkyl bromide compounds, such as methyl bromide. Methyl bromide is toxic and, if discharged into the atmosphere, is believed to contribute to depletion of atmospheric ozone. It is therefore important to avoid discharge of methyl bromide into the atmosphere. Additionally, when compressed air is used as the source of dioxygen, the gaseous effluent contains nitrogen gas and unreacted dioxygen.

The vaporized solvent, which is typically a mixture of water and low-molecular weight carboxylic acid, has heretofore been condensed in one or more overhead condenser apparatus and the condensate returned to the reaction mixture. However, since water is also present, at least part of the condensate is usually directed to a separation apparatus, typically a distillation column, to separate the water from the low molecular weight aliphatic acid solvent so that the water concentration in the reactor is maintained at a constant level. Constituents of the gaseous effluent that are not condensed are typically passed through a vapor phase oxidation unit to burn these volatile organic byproducts and form an environmentally acceptable effluent.

The high pressure offgas contains a considerable amount of energy. Although prior art processes have, to an extent, utilized some of the energy contained in the offgas by running the offgas through, for example, an expander or turbine, prior art processes did not fully utilize the energy available in this high pressure offgas. In prior processes, heat removal from the reaction mixture was accomplished by condensing a portion of the reaction overhead vapor to produce moderate pressure steam. The moderate pressure steam, in part, was used to recover energy by a steam turbine, and a part was used to separate water from acetic acid by distillation.

In WO 96/39595, International Application Number: PCT/GB96/01261, a process is proposed for energy recovery from effluent gas derived from production of terephthalic acid by subjecting the effluent gas to catalytic combustion to convert methyl bromide vapor to bromine and/or gaseous hydrogen bromide and passing the resulting gas stream through an energy conversion device such as a gas turbine under controlled conditions of pressure and temperature such that condensation of hydrogen bromide and/or bromine is prevented in the energy conversion device. Hydrogen bromide and bromine are potential corrosion-producing agents especially in a mixture with condensate. The application states that where the presence of any condensation of hydrogen bromide and/ or bromine is prevented in equipment downstream of the catalytic oxidation zone, such may be fabricated from relatively inexpensive materials. Following passage through the energy recovery system according to the application, however, the gas is contacted with a liquid in a scrubbing unit to reduce the hydrogen bromide and bromine content of the gas vented to the environment.

In U.S. Pat. No. 5,113,015 and 5,235,102 to Palmer et al. processes are provided for recovering acetic acid from methyl acetate wherein the methyl acetate is hydrolyzed catalytically to methanol and acetic acid in the same tower or column that is used to separate the hydrolysis products. Advantageously, in the catalytic distillation a catalyst-packing material comprising a rigid, cellular monolith or a rigid, cellular monolith coated with a catalytically-active material is employed. Preferred rigid, cellular monoliths are ceramic honey-comb monoliths.

Significantly, U.S. Pat. Nos. 5,113,015 and 5,235,102, and WO 96/39595 make no reference to any possibility for recovery of hydrogen bromide from an alkyl bromide compound by hydrolyzing the alkyl bromide compound to hydrogen bromide and corresponding alcohol.

In the past various molecular sieve compositions natural and synthetic have, however, been found to be useful for a number of hydrocarbon conversion reactions. Among these are alkylation, aromatization, dehydrogenation and isomerization. Among the sieves which have been used are Type A, X, Y and those of the MFI crystal structure, as shown in "Atlas of Zeolite Structure Types," Second Revised Edition 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-II (Chu, in U.S. Pat. No. 3,709,979), Zeolite ZSM-12 (Rosinski, et al., in U.S. Pat. No. 3,832,449), and others.

The art, therefore, needs an improved method for handling alkyl bromide compounds that are produced as co-products during exothermic, liquid-phase oxidation of aromatic feedstock compounds to aromatic carboxylic acids.

It is desirable that an improved process shall recover from the alkyl bromide compounds the bromine as hydrogen bromide which is a form of bromine useful in the liquid-phase oxidation reaction mixture.

Furthermore, because hydrogen bromide and bromine are potential corrosion-producing agents especially in a mixture with condensate, an improved process whereby the recovered hydrogen bromide is recycled directly to the liquid-phase oxidation is particularly desirable.

Advantageously, such improvements shall be combined in a process for preparing aromatic carboxylic acids by the exothermic, liquid-phase oxidation of an aromatic feedstock compound wherein the energy produced by the exothermic oxidation is efficiently recovered, and uses of water produced during the preparation of aromatic carboxylic acids are efficiently integrated into the process.

The present invention provides such an improved process.

SUMMARY OF THE INVENTION

This invention is a process for recovery of hydrogen bromide from one or more alkyl bromide compound by hydrolyzing the alkyl bromide compounds to hydrogen bromide and corresponding alcohol, and simultaneously separating at least the alcoholic products of hydrolysis from aliphatic monocarboxylic acid solvent. For example, hydrolyzing methyl bromide to hydrogen bromide and methanol and simultaneously separating the methanol product of hydrolysis from acetic acid.

Processes of this invention comprises contacting countercurrently in a high efficiency separation apparatus a gaseous stream comprising dioxygen, carbon monoxide, carbon dioxide, steam, aliphatic monocarboxylic acid of 2 to about 6 carbon atoms and one or more alkyl bromide compound of 1 to about 5 carbon atoms with an aqueous liquid phase in the presence of solid hydrolysis-promoting catalyst material to form products of the hydrolysis comprising an alcohol and hydrogen bromide, and separating aqueous hydrogen bromide and the less volatile aliphatic monocarboxylic acid from the more volatile alcohol in the high efficiency separation apparatus by volatility, the aqueous hydrogen bromide and aliphatic monocarboxylic acid being contained in the aqueous liquid phase, and the alcohol being carried up and out of the separation apparatus in a gaseous stream, the hydrolysis and separation being carried out coextensively in the separation apparatus.

In another aspect of this invention the high efficiency separation apparatus is a high efficiency distillation column, preferably having at least about 30 theoretical plates, and the solid hydrolysis promoting catalyst material is in the form of distillation column packing.

In another aspect of this invention the solid hydrolysis-promoting catalyst material includes an essentially hydrogen-form, crystalline molecular sieve having the MFI crystal structure. Generally, such solid hydrolysis-promoting catalyst material also includes one or more binder materials. Preferably the solid hydrolysis-promoting catalyst materials used in accordance with this invention include binder materials or matrix materials which comprise at least one member selected from the group consisting of titania, zirconia, silica, silica alumina, alpha-alumina, pseudo-boehmite, boehmite, gamma-alumina, and/or fluoropolymer resin selected from the group consisting of fluorohydrocarbon, chlorofluorohydrocarbon, chlorofluorocarbons fluorocarbon resins and mixtures thereof. Preferably silica, silica-alumina, or a fluorocarbon resin such as tetrafluoroethylene, is used as a binder.

Still another aspect is the process according to this invention wherein the gaseous stream is a high pressure overhead stream from an oxidation zone in a continuous process for preparing aromatic dicarboxylic acid by liquid-phase oxidation of a corresponding benzene compound having two oxidizable alkyl or acyl ring substituents or an oxidizable alkyl and acyl ring substituent in non-adjacent positions or a corresponding naphthalene having two oxidizable alkyl or acyl ring substituents or oxidizable alkyl and acyl ring substituent, with a dioxygen-containing gas in a solvent comprising the aliphatic monocarboxylic acid at an elevated temperature and pressure and in the presence of an oxidation catalyst comprising a heavy metal component and a source of bromine. Advantageously, the benzene compound being oxidized according to this invention is paraxylene and the aromatic dicarboxylic acid is terephthalic acid.

Yet another aspect is the process according to this invention wherein the aliphatic monocarboxylic acid is acetic acid, the overhead stream from the oxidation zone comprises dioxygen, carbon monoxide, carbon dioxide, steam, acetic acid, methyl acetate and at least methyl bromide, and both the methyl acetate and methyl bromide are hydrolyzed to methanol and acetic acid or hydrogen bromide by contacting with an aqueous liquid phase in the presence of the solid hydrolysis promoting catalyst material.

This invention is also a continuous process for preparing aromatic acid from a corresponding methyl substituted aromatic compound by catalytic liquid-phase oxidation of the methyl groups with a dioxygen-containing gas in a solvent comprising a lower aliphatic monocarboxylic acid at an elevated temperature and pressure and in the presence of an oxidation catalyst comprising a heavy metal component and a source of bromine, which process comprises: (a) oxidizing a methyl substituted aromatic compound to an aromatic carboxylic acid in a liquid-phase reaction mixture comprising water, aliphatic monocarboxylic acid of 2 to about 6 carbon atoms, an oxidation catalyst comprising a heavy metal component and a source of bromine and a source of dioxygen, under reaction conditions which produce a gaseous high pressure stream comprising dioxygen, carbon monoxide, carbon dioxide, steam, aliphatic monocarboxylic acid of 2 to about 6 carbon atoms and one or more volatile organic bromide compound; (b) contacting counter-currently in a high efficiency separation apparatus the gaseous stream with an aqueous liquid phase in the presence of solid hydrolysis-promoting catalyst material which does not disintegrate in less than one month under conditions employed in the separation apparatus to form products of the hydrolysis comprising an alcohol and hydrogen bromide, and separating aqueous hydrogen bromide and the less volatile aliphatic monocarboxylic acid from the more volatile alcohol in the high efficiency separation apparatus by volatility, the aqueous hydrogen bromide and aliphatic monocarboxylic acid being contained in the aqueous liquid phase withdrawn from the separation apparatus in a liquid bottoms stream and the alcohol being carried up and out of the separation apparatus in a gaseous stream, the hydrolysis and separation being carried out coextensively in the separation apparatus.

In another aspect this invention is a continuous process for preparing dicarboxylic aromatic acid by liquid-phase oxidation of a corresponding benzene having two oxidizable alkyl or acyl ring substituents or an oxidizable alkyl and acyl ring substituent in non-adjacent positions or a corresponding naphthalene having two oxidizable alkyl or acyl ring substituents or oxidizable alkyl and acyl ring substituent, with a dioxygen-containing gas in a solvent at an elevated temperature and pressure and in the presence of an oxidation catalyst comprising a heavy metal component and a source of bromine, which process comprises: (a) oxidizing a substituted aromatic feedstock compound to an aromatic dicarboxylic acid in a liquid-phase reaction mixture comprising water, aliphatic monocarboxylic acid of 2 to about 6 carbon atoms, an oxidation catalyst comprising a heavy metal component and a source of bromine and a source of dioxygen, under reaction conditions which produce a gaseous high pressure stream comprising dioxygen, carbon monoxide, carbon dioxide, steam, aliphatic monocarboxylic acid and one or more alkyl bromide compound of 1 to about 5 carbon atoms; (b) contacting countercurrently in a high efficiency separation apparatus the gaseous stream with an aqueous liquid phase in the presence of solid hydrolysis-promoting catalyst material which does not disintegrate in less than one month under conditions employed in the separation apparatus to form products of the hydrolysis comprising an alcohol and hydrogen bromide, and separating aqueous hydrogen bromide and the less volatile aliphatic monocarboxylic acid from the more volatile alcohol in the high efficiency separation apparatus by volatility, the aqueous hydrogen bromide and aliphatic monocarboxylic acid being contained in the aqueous liquid phase withdrawn from the separation apparatus and the alcohol being carried up and out of the separation apparatus in a gaseous stream, the hydrolysis and separation being carried out coextensively in the separation apparatus; (c) separating the aromatic dicarboxylic acid formed in step (a) from reaction mother liquor produced during the liquid phase oxidation reaction mixture to form crude aromatic carboxylic acid; (d) purifying crude aromatic carboxylic acid at an elevated temperature and pressure in a purification solvent comprising water to form a mixture of purified aromatic carboxylic acid and purification mother liquor comprising water; and (e) separating purified aromatic carboxylic acid from purification mother liquor formed in step (d) and recycling at least a portion of the purification mother liquor to the high efficiency distillation column.

For a more complete understanding of the present invention, reference should now be made to the embodiments illustrated in greater detail in the accompanying drawings and described below by way of examples of the invention.

BRIEF DESCRIPTION OF THE DRAWINGS

The appended claims set forth those novel features which characterize the present invention The present invention itself, as well as advantages thereof, may best be understood, however, by reference to the following brief description of preferred embodiments taken in conjunction with the annexed drawing, in which:

BRIEF DESCRIPTION OF THE INVENTION

In the process of this invention an aromatic feedstock compound is oxidized in an exothermic, liquid-phase oxidation reaction mixture to an aromatic carboxylic acid, and the energy generated by this highly exothermic oxidation is efficiently recovered and used, for example, to generate electricity or other forms of useful and transmittable energy.

The aromatic feedstock compound useful in the process of this invention is any aromatic compound that has oxidizable substituents which can be oxidized to a carboxylic acid group. For example, the oxidizable substituent can be an alkyl group such as a methyl, ethyl, or isopropyl group. It can also be a partially oxidized alkyl group such as an alcohol group, aldehyde group or ketone group. The aromatic portion of the aromatic feedstock compound can be a benzene nucleus or it can be bi- or polycyclic, for example a naphthalene nucleus. The number of oxidizable substituents on the aromatic portion of the aromatic feedstock compound can be equal to the number of sites available on the aromatic portion of the aromatic feedstock compound, but is generally fewer, and is preferably 1 to about 4, more preferably 2 or 3. Thus, examples of suitable aromatic feedstock compounds for the process of this invention include toluene, ethylbenzene, ortho-xylene, meta-xylene, para-xylene, 1-formyl-4-methyl-benzene, 1-hydroxymethyl-4-methylbenzene, 1,2,4-trimethyl-benzene, 1-formyl-2,4-dimethylbenzene, 1,2,4,5-tetramethyl-benzene, alkyl, hydroxymethyl, formyl, and acyl substituted naphthalene compounds such as 2,6- and 2,7-dimethyl-naphthalene, 2-acyl-6-methylnaphthalene, 2-formyl-6-methyl-naphthalene, 2-methyl-6-ethylnaphthalene, 2,6-diethyl-naphthalene, and the like.

For example, para-xylene, when oxidized produces terephthalic acid, meta-xylene produces isophthalic acid and 2,6-dimethyinaphthalene produces 2,6-naphthalenedicarboxylic acid.

As mentioned hereinabove, methods for oxidizing aromatic feedstock to the corresponding aromatic carboxylic acid using a liquid-phase, heavy-metal catalyzed oxidation reaction are well known in the art. For example, Saffer et al. U.S. Pat. No. 2,833,816 discloses such processes. Other processes are disclosed in U.S. Pat. Nos. 3,870,754; 4,933,491; 4,950,786; and 5,292,934. A particularly preferred method for oxidizing 26-dimethylnaphthalene to 2,6-naphthalenedicarboxylic acid is disclosed in U.S. Pat. No. 5,183,933. However, in general, suitable heavy metal oxidation catalysts include those metals having an atomic number of about 21 to about 82, inclusive, preferably a mixture of cobalt and manganese. The preferred oxidation solvent is a low molecular weight aliphatic monocarboxylic acid having 2 to about 6 carbon atoms, inclusive, or mixtures thereof with water. Preferably it is acetic acid or mixtures of acetic acid and water. A reaction temperature of about 145° C. to about 235° C. is typical, and the reaction pressure is such that the reaction mixture is under liquid phase conditions. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required, and typically it is air. For the conversion of para-xylene to terephthalic acid the source of molecular oxygen can vary in molecular oxygen content from that of 10 percent molecular oxygen, to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the overhead gas-vapor mixture.

The catalyst employed in the oxidation step for producing crude terephthalic acid preferably comprises cobalt, manganese, and bromine components, and can additionally comprise accelerators known in the art. The ratio of cobalt (calculated as elemental cobalt) in the cobalt component of the catalyst-to-para-xylene in the liquid-phase oxidation is suitably in the range of about 0.2 to about 10 milligram atoms (mga) per gram mole of para-xylene. The ratio of manganese (calculated as elemental manganese) in the manganese component of the catalyst-to-cobalt (calculated as elemental cobalt) in the cobalt component of the catalyst in the liquid-phase oxidation is suitably in the range of about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is suitably in the range of about 0.2 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromine (for example HBr, NaBr, KBr, $NH_4Br$, etc.), or organic bromides which are known to provide bromide ions at the operating temperature of the oxidation (e.g. benzylbromide, mono- and di-bromoacetic acid. bromoacetyl bromide, tetrabromoethane, ethylene-dibromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means.

For the oxidation of para-xylene to terephthalic acid, the minimum pressure at which the oxidation reactor is maintained is typically that pressure which will maintain a substantial liquid phase of the para-xylene and the solvent. When the solvent is an acetic acid-water mixture, suitable reaction gauge pressures in the oxidation reactor are in the range of about 0 $kg/cm^2$ to about 35 $kg/cm^2$, and typically are in the range of about 10 $kg/cm^2$ to about 20 $kg/cm^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

Process conditions described hereinabove for oxidizing para-xylene to terephthalic acid can also be used to oxidize meta-xylene to isophthalic acid.

For the oxidation of 2,6-dimethylnaphthalene to 2,6-naphthalene-dicarboxylic acid the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1 and the total of cobalt and manganese, calculated as elemental cobalt and elemental manganese is at least about 0.40 weight percent based on the weight of the solvent, and the oxidation reaction temperature is about 185° C. to about 220° C. Acetic acid is the most suitable solvent for oxidation of 2,6-dimethylnaphthalene.

The reactor vessel used for conducting the liquid phase oxidation of the aromatic feedstock compound to the aromatic carboxylic acid is any reactor vessel that is designed to operate at the reaction conditions used for the liquid-phase oxidation reaction. Typically these reactors are constructed of an inert material such as titanium, or are lined with an inert material such as glass or titanium. If the oxidation reaction is conducted at an elevated pressure, the reactor must also be constructed to withstand the pressures used for the oxidation reaction. The reactor can also be equipped with one or more agitators. Generally, the reactor is of a cylindrical design and is positioned in a vertical manner.

As stated hereinabove, the heat generated during the liquid-phase oxidation is dissipated by allowing the reaction solvent to vaporize from the reaction mixture along with the water present in the reaction mixture. Since the temperature at which a liquid boils is related to the pressure; the temperature of the oxidation reaction can be controlled by controlling the reaction pressure. At a reaction pressure of about 7 to about 21 $kg/cm^2$, the temperature of the reaction mixture using acetic acid as the solvent, and the vapor produced therefrom, is about 170° C. to about 210° C. Thus, the high temperature, high pressure vapor generated by the liquid phase oxidation reaction is a considerable source of energy, particularly when one considers the amount of such vapor produced in a large-scale commercial plant producing 200,000 to 750,000 metric tons of aromatic carboxylic acid per year.

In the process of this invention, the vaporized reaction solvent is directed to an apparatus, such as a high efficiency distillation column, that can separate the solvent, typically low molecular weight aliphatic carboxylic acid, from the water produced during the oxidation reaction. For reasons discussed in more detail below, the apparatus used for separating the water from the solvent must be able to make a separation such that at least about 95%, more preferably about 98% and most preferably at least about 99% by weight of the low molecular weight carboxylic acid solvent in the vaporous oxidation reaction stream is removed. Thus, the gaseous stream exiting the separation apparatus has a very low level of reaction solvent and, except for carbon oxides, nitrogen and oxygen gas and any by-products, it is mainly high pressure steam. For example, when the reaction solvent is a low molecular weight carboxylic acid such as acetic acid, the vapor entering the separation apparatus comprises a mixture of acetic acid and water wherein the ratio of acetic acid to water, by weight, is about 20:1 to about 3:1, and the vapor exiting the separation apparatus is generally less than about 0.5 weight percent acetic acid, more preferably less than about 0.1 weight percent acetic acid and most preferably less than about 0.05 weight percent acetic acid.

Although the apparatus used to conduct this separation can be any apparatus that can separate water from the reaction solvent the preferred apparatus or means for conducting such a separation is a distillation column, preferably a high-efficiency distillation column. Any high efficiency distillation column can be used; however, preferable distillation columns are those containing a high efficiency packing such as Koch Flexipac and the like or containing sieve valve or bubble cap trays. Preferably, the distillation column has at least about 30 theoretical plates, more preferably, at least about 50 theoretical plates. The distillation column must be able to make a separation such that at least 95%, more preferably about 98% and most preferably at least about 99% by weight of the low molecular weight carboxylic acid solvent in the vaporous overhead oxidation reaction stream is removed. As stated above, in these overhead streams, the ratio of low molecular weight monocarboxylic acid, such as acetic acid, to water, by weight, is typically about 20:1 to about 2:1.

Preferably, the separation apparatus is designed to make the separation of the reaction solvent from water at elevated pressure. The separation apparatus is preferably operated at a pressure equal to or slightly below the pressure of the liquid phase oxidation reaction.

Any means can be used to direct the vapor produced by the liquid phase oxidation reaction to the separation apparatus. For example, piping or other suitable conduit can be used. Additionally, the separation apparatus, such as a distillation column, can be directly connected to the reactor vessel used to conduct the liquid phase oxidation reaction.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Zeolitic materials, both natural and synthetic, useful herein have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

The molecular sieve useful in this invention can be prepared by crystallizing an aqueous mixture, at a controlled pH, of sources for cations, an oxide of aluminum, an oxide of silicon, and an organic template compound.

Manufacture of the ZSM materials utilizes a mixed base system in which sodium aluminate and a silicon containing material are mixed together with sodium hydroxide and an organic base, such as tetrapropylammonium hydroxide and tetrapropylammonium bromide, under specified reaction conditions, to form the crystalline aluminosilicate.

Typically, the molar ratios of the various reactants can be varied to produce the crystalline aluminosilicates of this invention. Specifically, the molar ratios of the initial reactant concentrations are indicated below:

| Reactants | Broad Preferred | Most Preferred | |
| --- | --- | --- | --- |
| $SiO_2/Al_2O_3$ | 5–400 | 10–150 | 40–120 |
| $R_2O^+/[R_2O^+ + M_{2/n}O]$ | 0.1–1.0 | 0.2–0.97 | 0.2–0.9 |
| $OH^-/SiO_2$ | 0.01–11 | 0.02–2 | 0.03–1 |
| $H_2O/OH^-$ | 10–4000 | 10–500 | 10–500 | wherein R is an organic compound and M is at least one cation having the oxidation state n, such as an alkali or an alkaline earth metal cation or hydrogen. By regulation of the quantity of aluminum (represented as $Al_2O_3$ in the reaction mixture), it is possible to vary the $SiO_2/Al_2O_3$ molar ratio in the final product.

More specifically, the sieve material useful in the present invention may be prepared by mixing a base, an aluminum oxide source, and an organic template compound in water (preferably distilled or deionized). The order of addition usually is not critical although a typical procedure is to dissolve base and sodium aluminate in water and then add the template compound. Generally, the silicon oxide compound is then added with intensive mixing such as that performed in a Waring blender and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH-/SiO_2$ shown above should furnish a pH of the system that broadly falls within the range of about 9 to about 13.5. Advantageously, the pH of the reaction system falls within the range of about 10 to about 11.

Examples of materials affording silicon oxide useful in this invention include silicic acid, sodium silicate, tetraalkyl silicates and Aerosil-380, a product of Degussa AG. Typically, the oxide of aluminum source is sodium aluminate.

Cations useful in formation of crystalline aluminosilicate include alkali metal and alkaline earth metal cations such, as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. If a base such as ethylenediamine is used, the hydrogen form of the sieve can be made directly.

Organic templates useful in preparing crystalline aluminosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more preferred description of a typical preparation of this invention, suitable quantities of sodium hydroxide and silica are dissolved with intense mixing in distilled or deionized water followed by addition of the organic template. The sodium aluminate is then slowly added with mixing. The pH is adjusted to about 10.5+−0.05 using a compatible acid such as sulfuric acid or base.

Alternatively and more preferably, crystalline aluminosilicate molecular sieve can be prepared by crystallizing a mixture of sources for an oxide of silicon, an oxide of aluminum, an alkyl ammonium compound and ethylenediamine such that the initial reactant molar ratios of water to silica range from about 1 to about 20, preferably about 3 to about 10 and most preferably from about 4 to about 6. In addition, preferable molar ratios for initial reactant silica to oxide of aluminum range from about 4 to about 150, more preferably from about 5 to about 120 and most preferably from about 5 to about 80. The molar ratio of ethylenediamine to silicon oxide should be above about 0.01, typically below 11, preferably between about 0.01 and about 2.0 and most preferably between about 0.02 and 1. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1 and most preferably about 0.02 to about 0.08.

The resulting slurry is transferred to a closed crystallization vessel and reacted usually at a pressure at least the vapor pressure of water for a time sufficient to permit crystallization which usually is about 0.25 to about 20 days, typically about one to about ten days and preferably about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 150° C. for about two to five days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 120° C. for about 16 hours and is then calcined in air in a manner such that the temperature rise does not exceed 125° C. per hr until a temperature of about 550° C. is reached. Calcination at this temperature usually is continued for about 4 to 16 hours.

A preferred class of molecular sieves useful, according to the present invention, are crystalline borosilicate molecular sieves disclosed in commonly assigned U.S. Pat. Nos. 4,268,420, U.S. Pat. No. 4,269,813, U.S. Pat. No. 4,292,457, and U.S. Pat. No. 4,292,458 to Marvin R. Klotz, which are specifically incorporated herein in their entirety by reference.

Alternatively crystalline borosilicate molecular sieves useful in this invention, can be prepared by crystallizing an aqueous mixture, at a controlled pH, of sources for cations, an oxide of boron, an oxide of silicon, and an organic template compound as described in U.S. Pat. No. 5,053,211 to Muin S. Haddad, the disclosure of which is specifically incorporated herein in its entirety by reference.

Suitable for use according to the present invention are, broadly, crystalline borosilicates which comprise a molecular sieve material having the following compositions in terms of mole ratios of oxides:

$$0.9 \pm 0.2 M_{2/n}O : B_2O_3 : Y\ SiO_2 : Z\ H_2O,$$

where M is at least one cation having a valence of n, Y is between 4 and about 600, and Z is between 0 and about 160.

Embodiments of these borosilicates are prepared by the method which comprises: (1) preparing a mixture containing an oxide of silicon, an oxide of boron, a hydroxide of an alkali metal or an alkaline earth metal, an alkyl ammonium cation or a precursor of an alkyl ammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

Catalytically active metals are placed onto the crystalline metalosilicate sieve by ion exchange, impregnation, a combination thereof, or other suitable contact means. Before placing the catalytically active metals on the aluminosilicate sieve or borosilicate sieve, the metalosilicate sieve is desirably in the hydrogen form. If the sieve was prepared using a metal hydroxide, such as sodium hydroxide, the hydrogen form typically is produced by exchanging one or more times with ammonium ion, typically using ammonium nitrate, followed by drying and calcination as described above. Ion exchange and impregnation techniques are well-known as can be understood by one skilled in the art. Amounts of catalytically active metals, such as platinum, placed on the metalosilicate sieve can vary individually from about 0.01 weight percent to about 5 weight percent, typically from about 0.1 weight percent to about 1 weight percent, and most preferable 0.1 weight percent to 0.5 weight percent.

With or without active metal-loading, crystalline molecular sieves useful in this invention can be admixed with or incorporated within various binders or matrix materials depending upon the intended process use. Crystalline aluminosilicate sieve and/or crystalline borosilicate sieve can be combined with active or inactive materials, synthetic or naturally-occurring zeolites, as well as inorganic or organic materials which would be useful for binding the crystalline molecular sieve. Suitable binders or matrix materials include silica, aluminas, magnesia, titania, zirconia, alumina sols, hydrated aluminas, clays such as bentonite or kaolin, polymeric resins such as fluoropolymers, or other binders well-known in the art.

Typically, the metalosilicate is incorporated within a matrix material by blending with a sol of the matrix material and gelling the resulting mixture. Also, solid particles of the metalosilicate and matrix material can be physically admixed. Typically, such metalosilicate compositions can be pelletized or extruded into useful shapes. The crystalline metalosilicate content can vary anywhere from a few up to 100 weight percent of the total composition. Catalytic compositions can contain about 0.1 weight percent to about 100 weight percent crystalline metalosilicate material and preferably contain about 10 weight percent to about 95 weight percent of such material and most preferably contain about 20 weight percent to about 80 weight percent of such material.

Fluoropolymer resins are a well known family of polymers based on organic fluorochemicals which include fluorohydrocarbon, chlorofluorohydrocarbon, chlorofluorocarbon, and fluorocarbon resins. See, for example, D. C. Miles and J. H. Bristion, *Polymer Technology*, Chemical Publishing Co., New York, 1979, pp 357 to 370, or C. A. Harper, ed., *Handbook of Plastice and Elastomers,* McGraw-Hill, New York, 1975, pp1–75 to 1–78. The original, basic fluorocarbon resin, and representative of the family, is tetrafluoroethylene (TFE). Other widely known fluoropolymer resins include, for example, fluoroinated ethyleneproplylene (FEP), ethylenetrafluoroethylene copolymer (ETFE), perfluoroalkoxy (PFA), chlorotrifluoroethylene (CTFE), ethylene-chlorotrifluoroethylene copolymer (E-CTFE), vinylidene fluoride ($PVF_2$), and polyvinylfluoride (PVF).

Hydrolysis in the presence of the above-described catalyst compositions is effected by contact of a gaseous mixture in a high efficiency separation apparatus at conditions of temperature and pressure therein which are suitable for separation by volatility of water produced during the oxidation reaction from the low molecular weight aliphatic carboxylic acid component of the oxidation reaction solvent. Reactions generally takes place at elevated pressure, but the pressure may be within the approximate range of about 1 bar to about 30 bar, more preferably between about 10 bar and about 15 bar. Reaction is suitably accomplished utilizing a superficial residence time of between about 1 seconds to about 100 seconds, preferably between about 2 seconds and about 50 seconds, and more preferably between about 2 seconds and about 10 seconds.

Thus, the vapor produced by the liquid phase oxidation reaction, along with any byproduct gases formed as a result of the oxidation, any carbon oxides formed during the oxidation and, if air is used as the source of molecular oxygen, nitrogen gas, are passed through the separation apparatus to remove most of the reaction solvent. The gas exiting the separation apparatus therefore generally comprises water (steam), carbon oxides, nitrogen gas, any unconsumed molecular oxygen, and oxidation reaction byproducts such as methyl bromide. Significantly, the gas exiting the separation apparatus is still at a high pressure and is, therefore, a valuable source of energy. While this offgas from the separation apparatus can be sent to a means for recovering energy, e.g. an expander, it is preferable to first remove corrosive and/or combustible byproduct materials from the high pressure offgas before it is directed to an expander or other means for energy recovery. While any means for removing combustible materials from the offgas is suitable, for example, a thermal oxidizer, a preferred method is to use a catalytic oxidation apparatus wherein the offgas is contacted with a suitable catalytic material at high temperature and high pressure in the presence of air or other source of molecular oxygen, and the corrosive and combustible byproduct materials in the offgas are catalytically oxidized to environmentally compatible materials. Such a catalytic oxidation unit can reduce or eliminate through oxidation, any residual oxidation reaction solvent present in the offgas, and it can oxidize a byproduct such as methyl bromide. However, in the method of this invention, the separation apparatus used removes most of the reaction solvent from the reaction offgas. Thus, the offgas entering the offgas catalytic oxidation unit has a low level of reaction solvent so the load on the catalytic oxidation unit is small. Otherwise, a high load of reaction solvent on the offgas catalytic oxidation unit would result in an excessively large temperature rise in the catalytic oxidation unit. Furthermore, the combustion of the reaction solvent would be a great economic loss since it is desirable to conserve and recycle as much of the oxidation reaction solvent as possible. Generally, the effluent from the catalytic oxidation unit is directed to a scrubber to remove any acidic, inorganic materials such as bromine and hydrogen bromide. Bromine and hydrogen bromide would be formed by the catalytic oxidation of methyl bromide. Oxidation catalysts for such offgas oxidation are available, for example, from Johnson Matthey, Engelhard Corp. or Allied Signal Inc.

The gaseous, high pressure effluent from the catalytic oxidation unit and scrubber is preferably directed to a pre-heater to elevate the temperature of the offgas and thereby convert any condensed water that may be present to steam. The dry, high pressure gas stream exiting the pre-heater is directed to an expander or other means for recovering energy from the high pressure gas stream.

The means for recovering energy from the high pressure offgas, e.g. an expander, is suitably connected to an electric generator and/or to other equipment requiring mechanical work such as a compressor. The electrical energy produced by a generator can be used to power the equipment used in the plant for manufacturing the aromatic carboxylic acid, for example, it can be used to operate compressors for adding air to the liquid phase oxidation reaction, and any excess electrical energy can be transmitted to a local electric power utility. For the production of terephthalic acid from paraxylene feedstock, the amount of energy recovered in the process of this invention is at least about 0.3 and more preferably at least about 0.35 kilowatt hours per pound of terephthalic acid produced.

After exiting the expander, the offgas is condensed and the resulting water is useful in other processes within the manufacturing plant. This water is of relatively high purity containing only a small amount of dissolved gases. For example, the condensed water can be used as a reflux for a distillation column used as a high efficiency separation apparatus. The water produced by the condensation of the offgas can also be used as the solvent for a purification step where the crude aromatic carboxylic acid is treated to a purified aromatic carboxylic acid. Thus, the water formed by the condensation from the reaction offgas can be used as a recrystallization solvent or as a solvent for conducting one or more chemical and/or physical treatments for the crude aromatic carboxylic acid. One such purification process comprises contacting an aqueous solution or slurry of the crude aromatic carboxylic acid with hydrogen at an elevated temperature and pressure in the presence of a hydrogenation catalyst. Such a process is disclosed in U.S. Pat. No. 3,584,039 to Meyer. Using the purification of terephthalic acid as an example, this purification procedure is conducted at an elevated temperature and pressure in a fixed catalyst bed. Both down-flow and up-flow reactors can be used. The crude terephthalic acid to be purified is dissolved in water or a mixture of water and some other polar solvent such as a $C_1$–$C_4$ aliphatic carboxylic acid.

The reactor, and thus the terephthalic acid solution temperature during purification, can be in the range of about 100° C. to about 350° C. Preferably the temperatures are in the range of about 275° C. to about 300° C.

Reactor pressure conditions primarily depend upon the temperature at which the purification process is carried out. Inasmuch as the temperatures at which practical amounts of the impure terephthalic acid may be dissolved are substantially above the normal boiling point of the solvent, the process pressures are necessarily considerably above atmospheric pressure to maintain the aqueous solutions in liquid phase. In general, the reactor pressure during hydrogenation can be in the range of about 200 to about 1500 pounds per square inch gauge (psig), and usually is in the range of about 900 psig to about 1,200 psig. The hydrogen partial pressure is typically in the range of about 30 psig to about 200 psig.

The catalyst used for this purification step comprises one or more active hydrogenation metals such as ruthenium, rhodium, palladium or platinum on a suitable support such as carbon or titania. A suitable support is an active carbon, usually derived from coconut charcoal in the form of granules having a surface area of 600 $m^2$/g to 1500 $m^2$/g. The loading of metal on the carrier is suitably about 0.01 weight percent to about 2 weight percent. Suitable materials for preparing purified aromatic carboxylic acids from crude aromatic carboxylic acids are disclosed in U.S. Pat. No. 5,256,817 to Sikkenga et al., and in U.S. patent application Ser. No. 029,037, filed on Mar. 10, 1993, to Schroeder et al.

After passing through the reactor for purifying the aromatic carboxylic acid, the solution of aromatic acid in aqueous solvent is cooled to precipitate the purified aromatic carboxylic acid. The temperature to which the solution is cooled is such that most of the purified aromatic carboxylic acid crystallizes. The crystallized purified aromatic carboxylic acid is separated from the aqueous mother liquor using a suitable solid-liquid separation device such as a centrifuge or filter. The cake of purified aromatic carboxylic acid can be washed with pure water, dried and sent to storage or for packaging and shipment.

The aqueous mother liquor separated by the centrifuge or filter contains a number of impurities, reaction intermediates and also contains suspended and dissolved aromatic carboxylic acid. In prior processes, this stream would be sent to a waste treatment facility. However, in the process of this invention, a major portion of this mother liquor can be diverted to the separation apparatus used for separating the oxidation reaction solvent from the water produced during the oxidation reaction. Thus, the impurities, reaction intermediates and aromatic carboxylic acid product are returned to the oxidation reaction mixture. Impurities are oxidized further, intermediates are converted to useful product, and aromatic carboxylic acid is recycled for recovery. Such a recycle of the mother liquor from the hydrogenation reaction is particularly useful when the separation apparatus used for separating water from the oxidation reaction solvent is a distillation column. The recycled aqueous mother liquor returned to the distillation column not only serves as reflux for the column, but also serves as an effective method for adding the mother liquor from the purification process to the oxidation reaction mixture. Thus the process of this invention provides for the elimination of a major waste product stream, a stream that would otherwise be sent to a waste treatment facility. Prior to recycling the mother liquor stream to the distillation column it can be treated to remove any suspended matter, if present. For example, it can be subjected to filtration or centrifugation, or it can be passed through a hydroclone to remove suspended matter. Prior to such treatment to remove suspended matter, the mother liquor can be treated, for example, by cooling, to remove dissolved compounds that might otherwise foul the distillation column.

Figure 1:
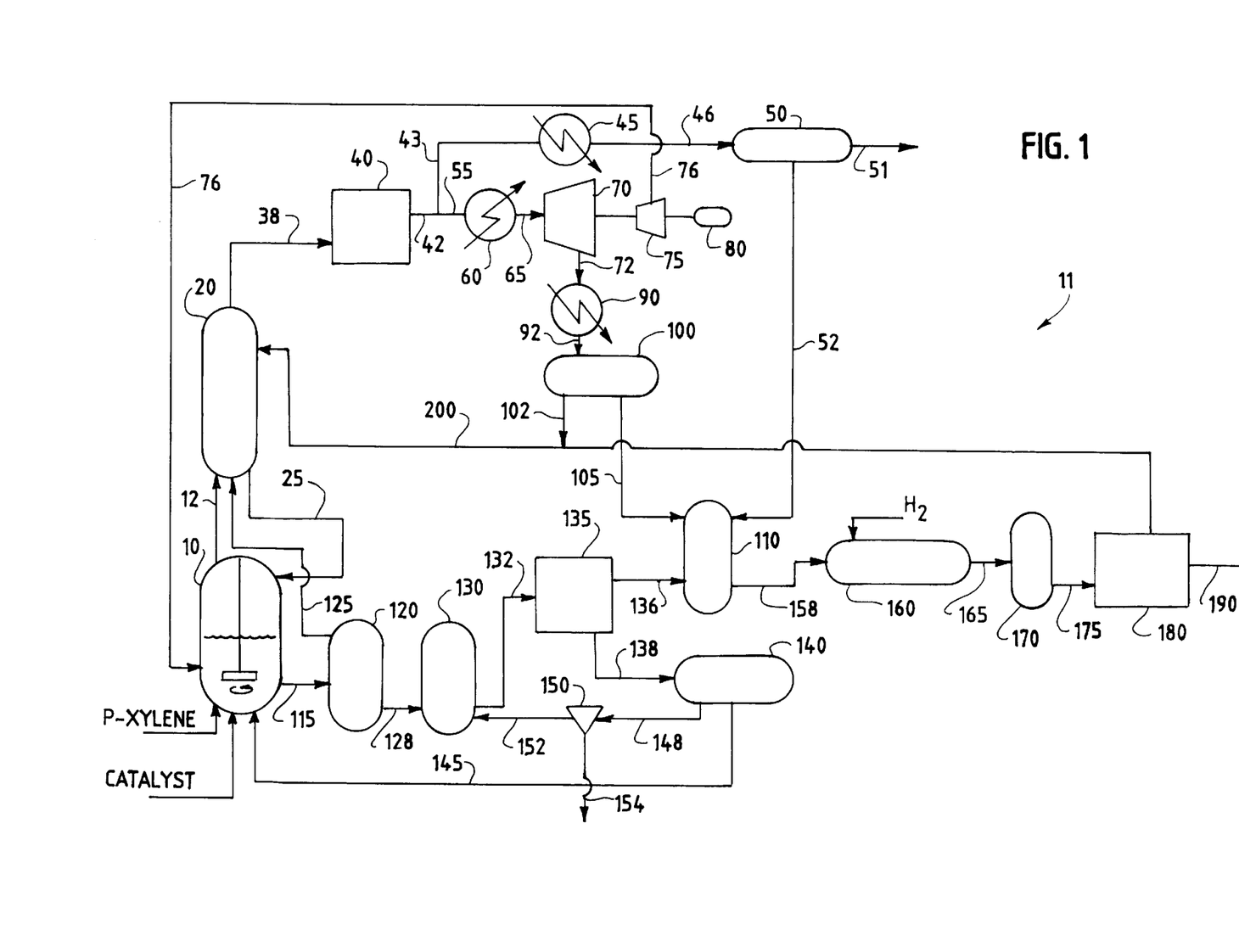
FIG. 1 is a simplified schematic diagram of a preferred method for operating the process of this invention in the continuous mode being arranged to provide sufficient reactants for the reactions and to maintain suitable reaction temperatures in accordance with the present invention.

FIG. 1 shows in schematic form a preferred embodiment 11 for operating the process of this invention. In agitated oxidation reactor 10 para-xylene is reacted with air in the presence of acetic acid and water as the oxidation solvent, cobalt and manganese oxidation metals and one or more bromine compounds such as hydrogen bromide as an oxidation promoter. The oxidation reaction is conducted at temperatures in a range of about 170° C. to about 210° C., and at pressures in a range of about 7 to about 21 kg/$cm^2$. Heat generated by the exothermic oxidation reaction causes the reactor solvent to boil- Vaporized solvent along with methyl bromide, methyl acetate and other volatile organic compounds, carbon oxides, nitrogen from the air charged to the oxidation reaction, and unreacted dioxygen pass through pipe 12 and into high pressure distillation column 20 having about 45 theoretical plates.

In the distillation column, acetic acid solvent is separated from the reaction overhead effluent or off-gas. The distillation column is constructed and operated such that at least 99 percent of the acetic acid is removed from the overhead gas. Acetic acid solvent in a liquid bottom stream from distillation column 20, which may contain some water, is returned to reactor 10 through pipe 25. The amount of solvent returned is controlled so that the proper amount of reaction solvent is maintained in the oxidation reactor.

In accordance with this invention at least a portion of distillation column 20 is provided with a hydrolysis-promoting catalytic-packing material wherein both methyl acetate and methyl bromide are hydrolyzed to methanol and acetic acid or hydrogen bromide.

Overhead effluent exiting the top of the high pressure distillation column 20 through pipe 38 contains less than about 0.1% by weight acetic acid, and is primarily steam, but also contains nitrogen, carbon oxides, unreacted oxygen, and volatile organic compounds such as methanol. Overhead effluent from pipe 38 is treated in a catalytic oxidation unit 40 where volatile organic compounds such as methanol and any residual acetic acid in the overhead effluent are catalytically oxidized. If acetic acid were not efficiently removed from the oxidation reaction overhead, it would be oxidized in the catalytic oxidation unit resulting in an economic loss. Gases exiting the catalytic oxidation unit 40 are directed to pipe 42.

In accordance with the present invention, solid oxidation catalysts suitable for use in the catalytic oxidation unit comprise a combustion promoting metal deposed on a catalyst support. Suitable oxidation catalyst supports include at least one member of the group consisting of titania, zirconia, silica, silica alumina, alpha-alumina, pseudo-boehmite, boehmite, gamma-alumina. The combustion promoting metal can be the types used or generally known in the art to promote the oxidation of carbon monoxide to carbon dioxide in the presence of molecular oxygen. The metal can be in a combined form, such as an oxide, rather than being in the elemental state. The combustion promoting metal can comprise two or more catalytically-active metals either physically or chemically combined. Suitable combustion promoting metals for use in the process of the present invention are the transition group elements of the Periodic Table (IUPAC), preferably the Group VIII metals, preferably the precious metals, and more preferably at least one member of the group consisting of tungsten oxide, cerium oxide, tin oxide, vanadium oxide platinum, palladium and rhodium. Platinum is preferred by reason of its ability to sustain high activity for oxidation of carbon monoxide.

The percentage of combustion promoting metal to add to the oxidation catalyst used in the present invention is a function of catalyst cost and process effectiveness. The preferred concentration of promoter metal is that which achieves process objectives at minimum catalyst cost. Generally, the combustion promoting metal is a costly component of the oxidation catalyst. Higher metal concentrations and lower volume usage reduces the support and oxidation catalyst costs. Suitable metal concentrations on the combustion promoter catalyst of the present invention can range by weight from about 0.1 ppm to about 15,000 ppm, preferably from about 0.5 ppm to about 10,000 ppm, and more preferably from about 1 ppm to about 8,000 ppm for best results.

Several particularly useful waste gas oxidation catalysts have been described. For example, U.S. Pat. No. 3,378,334, the disclosure of which is specifically incorporated herein in its entirety by reference, describes a fixed bed of spherical catalyst particles containing up to about 5 percent of a catalytically active metal. Suitable catalysts containing ruthenium, ruthenium plus platinum and platinum dispersed on a non-oxidizing support are described respectively in U.S. Pat. Nos. 4,059,675, 4,059,676 and 4,059,683, the disclosures of which are specifically incorporated herein in their entirety by reference.

At least a major portion of the gases from pipe 42, which comprise, primarily, acetic acid depleted steam at elevated pressure, are directed to pre-heater 60 through pipe 55. In pre-heater 60, the gases are heated further to temperatures of about 200° C. to about 235° C. and sufficient to prevent condensation in expander 70. Pre-heated gases enter expander 70 through pipe 65. Expander 70 is adapted to remove mechanical energy from the gases by expansion thereof and to produce an exhaust stream which exits expander 70 through conduit 72. The mechanical energy can be used, for example, to drive compressor 75 which delivers compressed air to oxidation reactor 10 through pipe 76. Preferably, a portion of the mechanical energy produced by the expander is used to drive electric generator 80 which supplies electric power for use within the TA manufacturing plant and to the local power utility Another portion of the gases from pipe 42 may, optionally, be directed to pipe 43 and then to condenser 45 where water is condensed from the gases. Cooled gas is directed to knock-out drum 50 through pipe 46. The water depleted gas exits the process through pipe 51. Water from knock-out drum 50 is directed to PTA slurry vessel 110. Where most, if not all, of the gases from pipe 42 are directed to the expander system, costs and expenses associated with the condenser 45 system can be reduced or avoided.

Expanded gases at reduced pressure exit expander 70 through pipe 72 and enter condenser 90 where steam in the expanded gases is condensed to liquid water. Water from condenser 90 is directed to reflux drum 100 through pipe 92. Water from drum 100 is directed to high pressure distillation column 20 through pipes 102 and 200. Such water returned to the column serves as reflux for the column. Water from drum 100 is also directed to PTA slurry vessel 110 through pipe 105.

A reaction mixture comprising crude terephthalic acid, water acetic acid, catalyst metals, oxidation reaction intermediate and by-products exits oxidation reactor 10 through pipe 115 and is directed to vessel 120 where the temperature of the oxidation reaction mixture is reduced to crystallize dissolved terephthalic acid. Vessel 120 is optionally equipped with an air sparger to continue the oxidation reaction. Gases from vessel 120 are directed to high pressure distillation column 20 having about 45 theoretical plates through pipe 125.

Slurry from vessel 120 is directed to vessel 130 through pipe 128 wherein additional cooling and crystallization of terephthalic acid occurs. Slurry from vessel 130 enters separation apparatus 135 through pipe 132. Separation apparatus 135 is, typically, comprised of one or more centrifuges or filters. In separation apparatus 135, crude terephthalic acid is separated from the oxidation reaction mother liquor. Oxidation reaction mother liquor exits separation apparatus 135 through pipe 138 and enters mother liquor drum 140. A major portion of the mother liquor containing catalyst and acetic acid is recycled to oxidation reactor 10 through line 145. Another portion of the mother liquor is sent to stripper apparatus 150 through pipe 148 where acetic acid is removed and directed to vessel 130 through line 152. A bottoms stream from stripper 150 is sent to waste treatment through pipe 154.

Crude terephthalic acid separated from the oxidation reaction mother liquor is transferred by means of conveyor 136 to PTA slurry drum 110. and at least partially dissolved with water condensed from the overhead gases exiting the top of the high pressure distillation column 20.

A slurry of crude terephthalic acid and water from slurry drum 110 is directed to hydrogenation reactor 160 through pipe 158. In hydrogenation reactor 160, the crude terephthalic acid dissolved in water is treated with hydrogen at an elevated temperature, for example, about 260° C. to about 290° C., and elevated pressure to purify the crude terephthalic acid by, for example, reducing the levels of 4-carboxybenzaldehyde. Effluent from hydrogenation reactor 160 enters crystallization vessel 170 through pipe 165. A slurry of purified terephthalic acid and water formed in vessel 170 is directed to separation apparatus 180 through pipe 175. Purified terephthalic acid exits separation apparatus 180 through conduit 190. Separation apparatus 180 is generally comprised of a centrifuge or a rotary vacuum filter. Mother liquor from separation apparatus 180 which comprises water, dissolved and suspended purified terephthalic acid, and various intermediate and by-product compounds, is recycled to the top of high pressure distillation column 20 through pipe 200. Return of mother liquor from separation apparatus 180 to high pressure distillation column 20 allows for recycle of intermediates and by-products in the mother liquor to the oxidation reactor where they are either oxidized or converted to terephthalic acid. It also provides for the recycle of valuable terephthalic acid which would otherwise be sent to waste treatment, or which would require costly procedures for its recovery, and it eliminates treating large volumes of waste water in waste treatment facilities.

Figure 2:
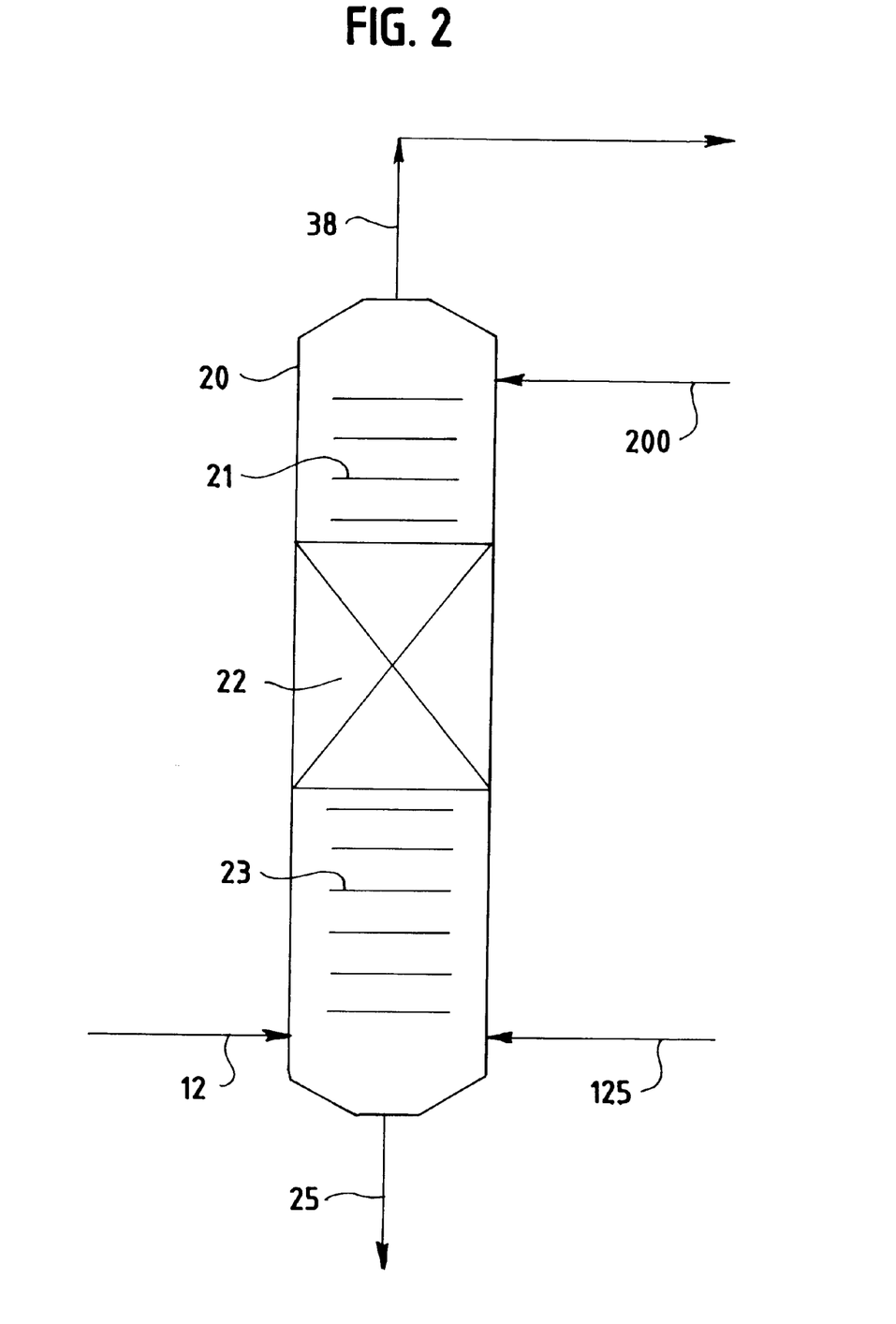
FIG. 2 is a simplified schematic diagram of a preferred high efficiency, continuous separation apparatus for contacting counter-currently a gaseous stream with an aqueous liquid phase in the presence of solid hydrolysis-promoting catalyst material.

In FIG. 2, high pressure distillation column 20 is depicted in somewhat greater detail. Catalyst zone 22 in column 20 contains solid hydrolysis promoting catalyst material in the form of distillation column packing, which may be present in one or more beds. The hydrolysis promoting catalyst material is that material which will catalyze the hydrolysis of organic material passing through catalyst zone 22. Above catalyst zone 22 the column is provided with an upper tray zone 21 and below catalyst zone 22 a lower tray zone 23. Alternatively, suitable conventional packing, such as Rashig rings, Pall rings, or saddles, and structured packing may be used in place of trays in either the upper zone 21 or the lower zone 23.

At a point below lower zone 23 a feedsteam containing vaporized solvent along with methyl bromide, methyl acetate and other volatile organic compounds, carbon oxides, nitrogen from the air charged to the oxidation reaction, and unreacted dioxygen from oxidation reactor 10 is introduced into high pressure distillation column 20 through pipe 12 where it contacts counter-currently a stream of liquid condensate from line 200. In column 20 both methyl acetate and methyl bromide are hydrolyzed to methanol and acetic acid or hydrogen bromide. The less volatile acetic acid and hydrogen bromide are retained in the liquid-phase, which is passed down through lower tray zone 23 and withdrawn from column 20 through pipe 25. The more volatile methanol is carried in up with other gases and non-condensibles through the upper tray zone 21 and out of column 20 through pipe 38.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

General

Hydrolysis experiments were conducted in a stainless steel column of 2.5 inch inside diameter and 60 inch height, which was provided with a gaseous feed preparation system, reservoir for liquid reflux solution, associated pumps, sample points, steam generation system and electrical heating units as required to maintain suitable conditions of hydrolysis. The column was operated as a trickle bed reactor where gas and liquid were contacted counter-currently in a bed of catalyst material. Liquid reflux solution was introduced at the top of the column. Heated gaseous feed entered at the bottom of the column. The column was operated at constant temperature of about 345° F. and a constant pressure of 185 psig. Catalysts were tested in the form of 1/16 inch extrudates.

Gaseous feed compositions were about 4 percent by volume of oxygen, 0.35 percent by volume of carbon monoxide, 1.4 percent by volume of carbon dioxide, from about 10 ppmv to about 1,000 ppmv each of methane, methyl acetate, methyl bromide and methanol, and a balance of nitrogen on a dry basis. Gaseous feed mixtures entering the column were about 2/3 steam. A superficial contact time was calculated as a ratio of catalyst bed volume to gaseous feed volume at standard conditions, 32° F. and 760 mm Hg.

Comparative Example

Equipment described above was used to conduct a series of hydrolysis experiments except that an inert packing material (stainless steel) was used to replace the catalyst bed. Conversions of methyl acetate and methyl bromide were determined at superficial residence times of about 57 seconds using water and two concentrations of aqueous acetic acid in the liquid reflux to the column. In Table I resulting hydrolysis conversions of methyl acetate and methyl bromide are presented for the three different reflux liquids.

TABLE I

| Reflux Acetic acid, Percent | Conversion of Methyl Acetate, Percent | Conversion of Methyl Bromide, Percent |
| --- | --- | --- |
| 0   | 13.7 | 24.0 |
| 0.8 | 14.3 | 22.3 |
| 5.0 | 20.4 | 24.3 |

Example 1

A series of hydrolysis experiments was conducted as described above using solid hydrolysis-promoting catalyst material containing a hydrogen-form, crystalline aluminosilicate molecular sieve having the MFI crystal structure with a silica binder. Amounts of 1/16 inch entrudates used were selected to provide superficial gas residence times from about 5 seconds to about 57 seconds. Acetic acid concentration in the reflux liquid was 0.8 percent by weight. In Table II resulting hydrolysis conversions of methyl acetate and methyl bromide are presented for the different superficial residence times.

TABLE II

| Residence Time, Seconds | Conversion of Methyl Acetate, Percent | Conversion of Methyl Bromide, Percent |
| --- | --- | --- |
| 5   | 95 | 16 |
| 10  | 97 | 28 |
| 40  | 94 | 69 |
| 57  | 94 | 81 |

Example 2

A series of hydrolysis experiments was conducted as described above using solid hydrolysis-promoting catalyst material containing a hydrogen-form, crystalline aluminosilicate molecular sieve having the MFI crystal structure with a silica binder. Amounts of 1/16 inch entrudates used were selected to provide superficial gas residence times of about 40 seconds and about 57 seconds. Acetic acid concentration in the reflux liquid was 5 percent by weight. In Table III resulting hydrolysis conversions of methyl acetate and methyl bromide are presented for the different superficial residence times.

TABLE III

| Residence Time, Seconds | Conversion of Methyl Acetate, Percent | Conversion of Methyl Bromide, Percent |
| --- | --- | --- |
| 40 | 84 | 68 |
| 57 | 78 | 80 |

Example 3

Equipment described above was charged with solid hydrolysis-promoting catalyst material containing a hydrogen-form, crystalline aluminosilicate molecular sieve having the MFI crystal structure with a silica binder. The amount of 1/16 inch entrudates used provide a superficial gas residence time of about 5 seconds. Water was the reflux liquid. Resulting hydrolysis conversions were 89.2 percent of methyl acetate and 15.8 percent of methyl bromide.

Example 4

Equipment described above was charged with solid hydrolysis-promoting catalyst material containing a hydrogen-form, crystalline borosilicate molecular sieve having the MFI crystal structure with an alumina binder (AMS-1B). Amounts of 1/16 inch entrudates used were selected to provide superficial gas residence times of about 10 seconds and about 40 seconds. The reflux liquid was water. In Table IV resulting hydrolysis conversions of methyl acetate and methyl bromide are presented for the different superficial residence times.

TABLE IV

| Residence Time, Seconds | Conversion of Methyl Acetate, Percent | Conversion of Methyl Bromide, Percent |
| --- | --- | --- |
| 10 | 68 | 27 |
| 40 | 96 | 69 |

For the purposes of the present invention, "predominantly" is defined as more than about fifty per cent. "Substantially" is defined as occurring with sufficient frequency or being present in such proportions as to measurably affect macroscopic properties of an associated compound or system. Where the frequency or proportion for such impact is not clear substantially is to be regarded as about twenty per cent or more. The term "Essentially" is defined as absolutely except that small variations which have no more than a negligible effect on macroscopic qualities and final outcome are permitted, typically up to about one percent.

Examples have been presented and hypotheses advanced herein in order to better communicate certain facets of the invention. The scope of the invention is determined solely by the scope of the appended claims.

Having described the invention, that which is claimed is:

1. A continuous process for preparing aromatic acid from a corresponding methyl substituted aromatic compound by catalytic liquid-phase oxidation of the methyl groups with a dioxygen-containing gas in a solvent comprising a lower aliphatic monocarboxylic acid at an elevated temperature and pressure and in the presence of an oxidation catalyst comprising a heavy metal component and a source of bromine, which process comprises:

(11-a) oxidizing a methyl substituted aromatic compound to an aromatic carboxylic acid in a liquid-phase reaction mixture comprising water, aliphatic monocarboxylic acid of 2 to about 6 carbon atoms, an oxidation catalyst comprising a heavy metal component and a source of bromine and a source of dioxygen, under reaction conditions which produce a gaseous high pressure stream comprising dioxygen, carbon monoxide, carbon dioxide, steam, aliphatic monocarboxylic acid, methyl ester thereof, and one or more volatile organic bromide compounds;

(11-b) contacting counter-currently in a high efficiency, continuous separation apparatus the gaseous stream with an aqueous liquid phase in the presence of solid hydrolysis-promoting catalyst material which does not disintegrate in less than one month under conditions employed in the separation apparatus to form products of the hydrolysis comprising an alcohol and hydrogen bromide, and separating aqueous hydrogen bromide and the less volatile aliphatic monocarboxylic acid from the more volatile alcohol in the high efficiency separation apparatus by volatility, the aqueous hydrogen bromide and aliphatic monocarboxylic acid being contained in the aqueous liquid phase withdrawn from the separation apparatus in a liquid bottoms stream and the alcohol being carried up and out of the separation apparatus in a gaseous high pressure overhead stream, the hydrolysis and separation being carried out coextensively in the continuous separation apparatus.

2. The process of claim 1 wherein the high efficiency separation apparatus is a high efficiency distillation column providing concentrations of aliphatic monocarboxylic acid in a high pressure overhead stream of less than about 1 percent by weight of the overhead stream, the solid hydrolysis promoting catalyst material is in the form of distillation column packing, and the catalyst material comprises an essentially hydrogen-form, crystalline molecular sieve having the MFI crystal structure and a binder material.

3. The process of claim 2 which further comprises directing the high pressure overhead stream to a means for recovering energy from the high pressure overhead stream.

4. The process of claim 3 wherein the means for recovering energy from the second high pressure overhead mixture is an expander.

5. The process of claim 4 wherein the expander drives an electric generator.

6. The process of claim 2 which further comprises directing the high pressure overhead stream to a means for increasing the energy content of the high pressure overhead stream by oxidation of the alcohol.

7. The process of claim 6 wherein the oxidation is carried out in the presence of a solid oxidation catalyst which comprises at least one member of the group consisting of titania, zirconia, silica, silica alumina, alpha-alumina, pseudo-boehmite, boehmite, gamma-alumina and optionally at least one member of the group consisting of tungsten oxide, cerium oxide, tin oxide, vanadium oxide, and the metals platinum, palladium and rhodium.

8. The process of claim 6 wherein the methyl substituted aromatic compound being oxidized is para-xylene, the aromatic carboxylic acid is terephthalic acid, the aliphatic monocarboxylic acid is acetic acid, the overhead stream from the oxidation zone comprises dioxygen, carbon monoxide, carbon dioxide, steam, acetic acid, methyl bromide, and methyl acetate which is substantially hydrolyzed to methanol and acetic acid during the countercurrent contacting with an aqueous liquid phase in the presence of a solid hydrolysis promoting catalyst material comprising an essentially hydrogen-form, crystalline molecular sieve having the MFI crystal structure and a binder material.

9. The process of claim 8 wherein the solid hydrolysis promoting catalyst material is in the form of distillation column packing, the molecular sieve is selected from the group consisting of aluminosilicate and borosilicate molecular sieves, and the binder material comprises at least one member selected from the group consisting of silica, silica-alumina, fluoropolymer resins.

10. The process of claim 6 wherein condensate derived from the high pressure overhead stream is used as solvent for purification of the aromatic carboxylic acid.

11. A continuous process for preparing dicarboxylic aromatic acid by liquid-phase oxidation of a corresponding benzene having two oxidizable alkyl or acyl ring substituents or an oxidizable alkyl and acyl ring substituent in non-adjacent positions or a corresponding naphthalene having two oxidizable alkyl or acyl ring substituents or oxidizable alkyl and acyl ring substituent, with a dioxygen-containing gas in a solvent at an elevated temperature and pressure and in the presence of an oxidation catalyst comprising a heavy metal component and a source of bromine, which process comprises:

(21-a) oxidizing a substituted aromatic feedstock compound to an aromatic dicarboxylic acid in a liquid-phase reaction mixture comprising water, aliphatic monocarboxylic acid of 2 to about 6 carbon atoms, an oxidation catalyst comprising a heavy metal component and a source of bromine and a source of dioxygen, under reaction conditions which produce a gaseous high pressure stream comprising dioxygen, carbon monoxide, carbon dioxide, steam, aliphatic monocarboxylic acid, ester thereof, and one or more alkyl bromide compound of 1 to about 5 carbon atoms;

(21-b) contacting counter-currently in a continuous, high efficiency separation apparatus the gaseous stream with an aqueous liquid phase in the presence of solid hydrolysis-promoting catalyst material which does not disintegrate in less than one month under conditions employed in the separation apparatus to form products of the hydrolysis comprising an alcohol and hydrogen bromide, and separating aqueous hydrogen bromide and the less volatile aliphatic monocarboxylic acid from the more volatile alcohol in the high efficiency separation apparatus by volatility, the aqueous hydrogen bromide and aliphatic monocarboxylic acid being contained in the aqueous liquid phase withdrawn from the separation apparatus and the alcohol being carried up and out of the separation apparatus in a gaseous, high pressure overhead stream, the hydrolysis and separation being carried out coextensively in the continuous separation apparatus;

(21-c) separating the aromatic dicarboxylic acid formed in step (21-a) from reaction mother liquor produced during the liquid phase oxidation reaction mixture to form crude aromatic carboxylic acid;

(21-d) purifying crude aromatic carboxylic acid at an elevated temperature and pressure in a purification solvent comprising water to form a mixture of purified aromatic carboxylic acid and purification mother liquor comprising water; and (21-e) separating purified aromatic carboxylic acid from purification mother liquor formed in step (21-d) and recycling at least a portion of the purification mother liquor to the high efficiency distillation column.

12. The process of claim 11 wherein the substituted aromatic feedstock compound being oxidized is para-xylene, the aromatic dicarboxylic acid is terephthalic acid, the aliphatic monocarboxylic acid is acetic acid, the overhead stream from the oxidation zone comprises dioxygen, carbon monoxide, carbon dioxide, steam, acetic acid, methyl bromide, and methyl acetate which is substantially hydrolyzed to methanol and acetic acid during the countercurrent contacting with an aqueous liquid phase in the presence of a solid hydrolysis promoting catalyst material comprising an essentially hydrogen-form, crystalline molecular sieve having the MFI crystal structure and a binder material.

13. The process of claim 12 wherein the solid hydrolysis promoting catalyst material is in the form of distillation column packing, the molecular sieve is selected from the group consisting of aluminosilicate and borosilicate molecular sieves, and the binder material comprises at least one member selected from the group consisting of silica, silica-alumina, fluoropolymer resins.

14. The process of claim 13 wherein the molecular sieve is an aluminosilicate molecular sieve having a Si/Al ratio of at least about 12, and the fluoropolymer resin is at least one member selected from the group consisting of fluorohydrocarbon, chlorofluorohydrocarbon, chlorofluorocarbon, fluorocarbon resins.

15. The process of claim 13 wherein the fluoropolymer resin is a polytetrafluoroethylene resin.

16. The process of claim 12 wherein the metalosilicate molecular sieve is a hydrogen-form of AMS-1 B crystalline borosilicate molecular sieve.

17. The process of claim 11 wherein the high efficiency separation apparatus is a high efficiency distillation column providing concentrations of aliphatic monocarboxylic acid in the overhead stream of less than about 1 percent by weight of the overhead stream, and the solid hydrolysis promoting catalyst material is in the form of distillation column packing.

18. The process of claim 11 wherein the purification solvent includes condensate derived from the high pressure overhead stream.

19. The process of claim 11 wherein the purification of the crude aromatic dicarboxylic acid is carried out in the presence of dihydrogen.

20. The process of claim 11 wherein at least most of the purification mother liquor is recycled to the high efficiency distillation column.

* * * * *